US00PP33715P2

(12) United States Plant Patent
Uebelhart

(10) Patent No.: US PP33,715 P2
(45) Date of Patent: Nov. 30, 2021

(54) ***HELIOPSIS* PLANT NAMED 'FUNKY SPINNER'**

(50) Latin Name: ***Heliopsis helianthoides* var. *scabra***
Varietal Denomination: Funky Spinner

(71) Applicant: Georg Uebelhart, Salzhausen (DE)

(72) Inventor: Georg Uebelhart, Salzhausen (DE)

(73) Assignee: JELITTO STAUDENSAMEN GMBH, Schwarmstedt (DE)

( * ) Notice: Subject to any disclaimer, the term of this patent is extended or adjusted under 35 U.S.C. 154(b) by 0 days.

(21) Appl. No.: 17/239,506

(22) Filed: Apr. 23, 2021

(51) Int. Cl.
*A01H 5/02* (2018.01)
*A01H 6/14* (2018.01)

(52) U.S. Cl.
USPC ..... Plt./437
CPC ..... *A01H 6/14* (2018.05)

(58) Field of Classification Search
USPC ..... Plt./437
CPC ..... A01H 6/14; A01H 5/02
See application file for complete search history.

*Primary Examiner* — Keith O. Robinson
(74) *Attorney, Agent, or Firm* — Penny J. Aguirre

(57) ABSTRACT

A new cultivar of *Heliopsis* plant named 'Funky Spinner' that is characterized by its short plant height (70 to 100 cm), depending on soil conditions, its stems that are sturdy and grey-purple to brown in color, its very dark green color foliage that is tinged black on the upper surface and slightly fading towards the end of the season, its medium sized inflorescences with ray florets that are yellow-orange in color with the lower ⅓$^{rd}$ of the ray florets orange-red to grey-purple in color, and its two, occasionally three whorls of ray florets.

2 Drawing Sheets

Botanical classification: *Heliopsis helianthoides* var. *scabra*.

Variety denomination: 'Funky Spinner'.

CROSS REFERENCE TO A RELATED APPLICATION

This application is related to a European plant breeders' rights application filed on Oct. 2, 2019, application No. 2019/2545. There have been no offers for sale anywhere in the world prior to the effective filing date of this Application and no accessibility to one of ordinary skill in the art could have been derived from the printed plant breeder's rights documents. This application is co-pending with a U.S. Plant Patent Application filed for a plant derived from the same breeding program that is entitled *Heliopsis* Plant Named 'Fire Twister' (U.S. Plant patent application Ser. No. 17/239,495).

BACKGROUND OF THE INVENTION

The present invention relates to a new and distinct cultivar of *Heliopsis* plant, botanically known as *Heliopsis helianthoides* var. *scabra* 'Funky Spinner' and will be referred to hereinafter by its cultivar name, 'Funky Spinner'.

'Funky Spinner' was derived from a controlled breeding program conducted by the Inventor in a nursery in Schwarmstedt, Germany. The breeding program focuses on obtaining new cultivars of *Heliopsis* with a sturdy, short plant habit, dark purple foliage and stems, bicolor inflorescences with yellow ray florets and strong red bases with more than one whorl of ray florets. 'Funky Spinner' was selected in summer of 2013 by the Inventor as a single unique plant derived from a cross made in 2012 between unnamed and unpatented proprietary plants from his breeding program; identified as sowing no. H10006.

Asexual propagation of the new cultivar was first accomplished using tissue culture using meristematic tissue under the direction of the Inventor in Rijswijk, The Netherlands in summer of 2015. Asexual propagation by stem tip cuttings, division and tissue culture has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Funky Spinner' as a unique cultivar of *Heliopsis*.

1. 'Funky Spinner' exhibits a short plant height (70 to 100 cm), depending on soil conditions.
2. 'Funky Spinner' exhibits stems that are sturdy and grey-purple to brown in color.
3. 'Funky Spinner' exhibits very dark green color foliage that is tinged black on the upper surface and slightly fading towards the end of the season.
4. 'Funky Spinner' exhibits medium sized inflorescences with ray florets that are yellow-orange in color with the lower ⅓$^{rd}$ of the ray florets orange-red to grey-purple in color.
5. 'Funky Spinner' exhibits two, occasionally three whorls of ray florets.

The female and male parent plants of 'Funky Spinner' both differ from 'Funky Spinner' in having a taller plant height, a floppy plant habit, small to medium sized inflorescences with less ray florets per inflorescence, and yellow-red to bicolor ray florets. 'Funky Spinner' can also be compared to *Heliopsis* cultivars 'Burning Hearts' (not patented), 'Summer Nights' (not patented) and 'Fire Twister'. 'Burning Hearts' and 'Summer Nights' are both similar to 'Funky Spinner' in having stems that are purple in color, disc florets that are dark in color, and a similar blooming period. 'Bleeding Hearts' differs from 'Funky Spinner' in having a much taller plant height, floppy plant habit, inflorescences that are small to medium in size with less ray florets, and ray florets that are yellow-red to bicolor. 'Summer Nights' differs from 'Funky Spinner' in having a much taller plant height, foliage that turns green in the summer, ray florets that are yellow with a halo of red at the base with a dark base, and variability in habit, flower size and flower color. 'Fire Twister' differs from 'Funky Spinner' in having inflorescences that open orange-red to grey-purple in color with a disc reddish in color and fading to orange, orange-red and grey-orange.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to Hayloft, Quilista Seed House, Green Trade Horticulture, Baldur-Garten, Mein Schoner Garten Shop, Kruglik, Anitra Perkins (facebook), Matelma, Kaufland, Schribergarten, Plant Estate, Dideli Nauji Gelynai, Prides Corner, Vitro Westland, All Plant Young Plants, Tuingoed Foltz, Tuinadvies, Haussermann, Hogendoorn, and Hortensia.

BRIEF DESCRIPTION OF THE DRAWINGS

The accompanying color photographs illustrate the overall appearance and distinct characteristics of the new *Heliopsis*. The photographs were taken of plants 7 months in age as field grown in Noordwijkerhout, the Netherlands.

The photograph in FIG. 1 provides a side view of a plant of 'Funky Spinner' in bloom.

Figure 1:
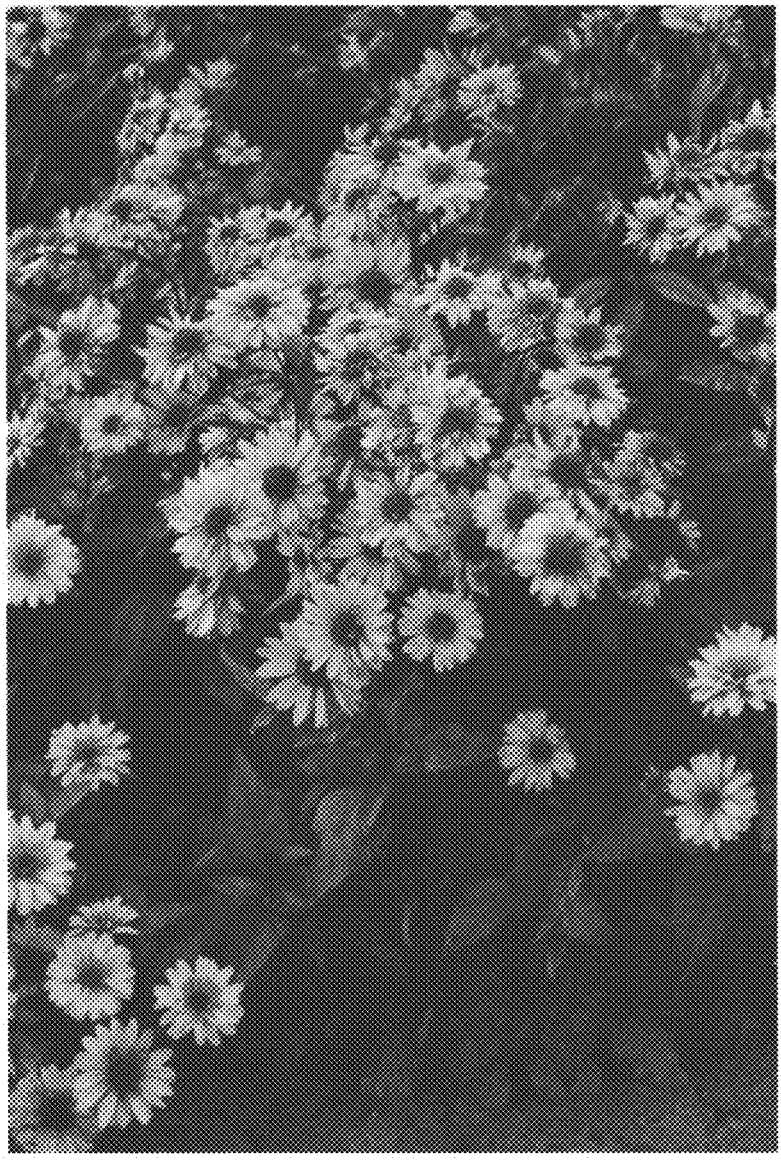
Figure 2:
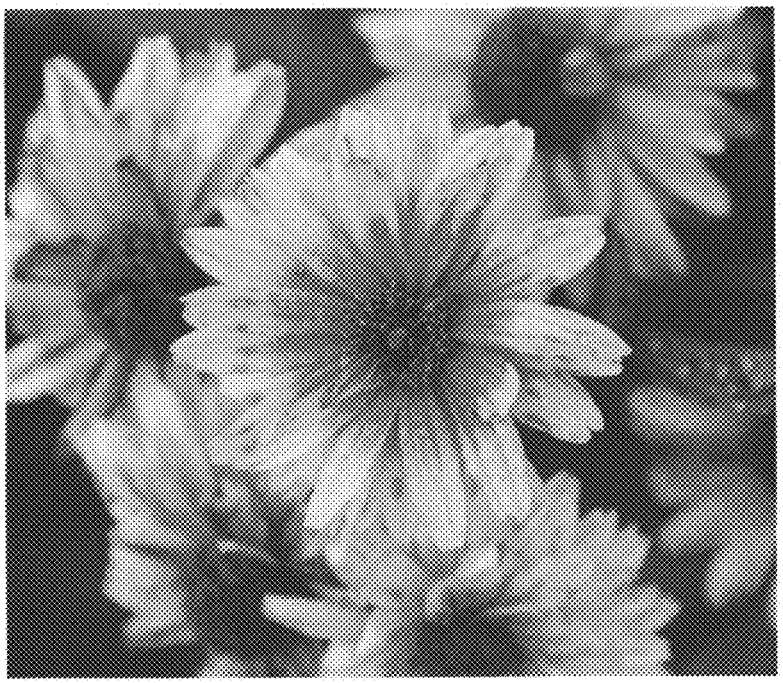

The photograph in FIG. 2 provides a close-up view of an Inflorescence of 'Funky Spinner'.

Figure 3:
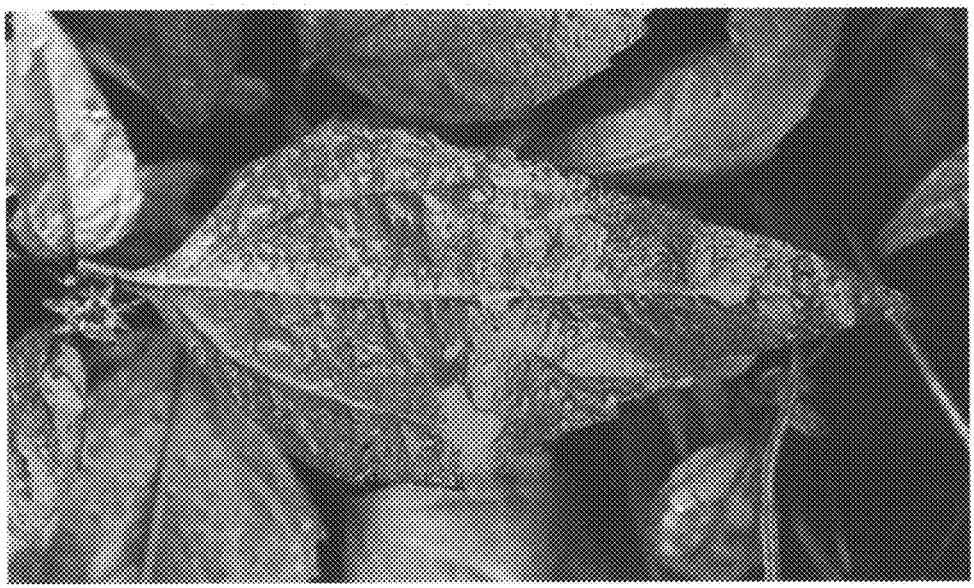

The photograph in FIG. 3 provides a close-up view of the foliage of 'Funky Spinner'.

The colors in the photographs are as close as possible with the photographic and printing technology utilized and the color values cited in the detailed botanical description accurately describe the colors of the new *Heliopsis*.

DETAILED BOTANICAL DESCRIPTION

The following is a detailed description of plants 7 months in age as field grown outdoors in September in Noordwijkerhout, the Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

- *Blooming season.*—8 weeks from late summer into autumn in The Netherlands.
- *Plant type.*—Herbaceous perennial.
- *Plant habit.*—Broadly spreading and upright.
- *Height and spread.*—Average of 80.5 cm in height (soil level to top of foliar plane), 89 cm in height (soil level to top of floral plane), and 77 cm in spread, reaches 70 to 100 cm in height and an average of 90 cm in spread in the landscape depending on soil conditions.
- *Hardiness.*—At least in U.S.D.A. Zones 4 to 9.
- *Diseases and pests.*—No susceptibility or resistance to diseases or pests has been observed.
- *Root description.*—Fibrous.
- *Propagation.*—Stem cuttings, tissue culture and division.
- *Root development.*—1 to 2 weeks for root initiation, a fully rooted young plant is produced in three to four weeks.
- *Growth rate.*—Moderate to highly vigorous.

Stem description:

- *Stem shape.*—Rounded and slightly angled, 5-sided.
- *Stem aspect.*—Main branches 50° from vertical, secondary branches 30° to main stem.
- *Stem strength.*—Moderately strong to strong.
- *Stem color.*—Young stems; N186C, mature stems; between 183A and 200B.
- *Stem surface.*—Young stems slightly pubescent covered with short adpressed hairs, hairs 0.5 mm in length, 156D in color, moderately glossy.
- *Branch size.*—Average of 20 cm in length, 4 mm in diameter.
- *Internode length.*—Average of 8.4 cm.
- *Branching.*—Freely branching, average of 5 main branches, 6 lateral branches per main branch.

Foliage description:

- *Leaf division.*—Simple.
- *Leaf shape.*—Ovate to broadly lanceolate.
- *Leaf base.*—Short, attenuate.
- *Leaf apex.*—Acute.
- *Leaf margin.*—Serrate.
- *Leaf venation.*—Pinnate, upper surface 177A, lower surface 197A to 197B.
- *Leaf attachment.*—Petiolate.
- *Leaf arrangement.*—Opposite.
- *Leaf surface.*—Both surfaces; rough to the touch due to strigose rugose, matte, both surfaces moderately covered with very short strigose hairs, average of 0.3 mm in length, 156D in color.
- *Leaf color.*—Young foliage upper surface; 137A, young foliage lower surface 138A, mature upper surface; NN137A, top tinged 203B, mature lower surface; 147B.
- *Leaf size.*—Average of 10 cm in length and 5.1 cm in width.
- *Petiole.*—Strong, an average of 1.9 cm in length and 3 mm in diameter, upper surface color 197A to 197B, lower surface color between 148A and 197A to 197B, both surfaces are matte and smooth, margins slightly covered with very short strigose hairs; 0.3 mm in length and too small to measure color.

Flower description:

- *Inflorescence type.*—Rotate, terminal capitulum consisting of a receptacle, disc florets and ray florets.
- *Lastingness of inflorescence.*—Average of 10 days, persistent.
- *Fragrance.*—Faint, sweet and slightly spicy.

*Quantity of inflorescences.*—2 per lateral stem, 160 inflorescences and buds per plant.

*Inflorescence buds.*—About 1.7 cm in depth and 1.6 cm in diameter, broad oblong to obovate in shape, immature ray florets pointing upward (near vertical), a blend of 151A and 177B, immature involucral bracts 147B, tinged 200B to 200C in color.

*Inflorescence size.*—About 2.4 cm in depth and 6.9 cm in diameter.

*Receptacle.*—Triangular, average of 9 mm in depth and 4 mm in diameter, disc diameter 1.4 cm, 145C in color.

*Peduncle.*—Round with axial ribs, 8.4 cm in length, 3 mm in diameter, strong, upright, straight on top of lateral branch, 200B, moderately glossy, sparsely covered with very short adpressed hairs, an average of 0.3 mm in length and too small to measure color.

*Involucral bracts* (*phyllaries*).—Rotate, broad ovate in shape, 30 per inflorescence, arranged in 2 rows, acute apex, broadly cuneate base, margin entire, upper surface color 145D, striped 144B, lower surface color 147A, base 200B, average of 6 mm in length, 4 mm in width, surfaces matte and covered with pubescence 0.3 mm in length, too small to measure color.

*Spine.*—Single bract present next to each individual disc floret, spirally placed on disc, one bract next to each individual disc floret, smooth and glabrous, 8 mm in length, 1 mm in diameter, narrow oblong in shape, obtuse apex, broadly cuneate base, moderately glossy, color; apex 178A, mid-section and base 155A.

Ray florets (carpellate):

*Number.*—Average of 50, 3 rows.

*Arrangement.*—Rotate.

*Appearance.*—Moderately carinate, nearly horizontal to slightly upward in an average of 10° to horizontal.

*Shape.*—Elliptic to oblanceolate.

*Aspect.*—Nearly horizontal.

*Size.*—Average of 3.5 cm in length and 9 mm in width.

*Petal apex.*—Shallow praemorse.

*Petal base.*—Attenuate.

*Petal margins.*—Entire.

*Petal texture.*—Upper surface velvety and matte, lower surface moderately velvety and very slightly glossy.

*Petal color.*—When opening upper surface and when fully open upper and lower surface; 17B, lower ⅓$^{rd}$ of ray florets orange-red to grey-purple, in between N34A and 185A, when opening lower surface 14A to 14B, upper and lower surface veins 17A to 17B, upper surface fading to 14A to 14B, lower ⅓$^{rd}$ 23A, lower surface fading to 14A to 14B.

Disc florets (perfect):

*Quantity.*—Average of 100.

*Shape.*—Tubular.

*Arrangement.*—Spirally placed on disc in 6 rows.

*Petal apex.*—Upper 12.5% free, acute, entire margins.

*Petal base.*—Lower 87.5% fused.

*Petal texture.*—Both surfaces glabrous, slightly glossy, non-rugose.

*Size.*—Average of 9 mm in length and 4 mm in width.

*Color.*—When opening upper and lower surface 183A, mid-section and base N163D, when fully open upper and lower surface 183A, mid-section and base 22A, changing to 22B at the base, both surfaces fading to 166C, mid-section and base 146C.

Reproductive organs:

*Presence.*—Disc flowers are perfect, ray flowers are carpellate.

*Gynoecium.*—Pistil; 1, per disc and ray floret, 7 mm in length, stigma; cleft, 3 mm in diameter, color 200A, style; 5 mm in length, 153D in color, ovary; 157C to 157D in color.

*Androecium.*—Stamens; 5 per disc floret, filaments; 4 mm in length and 155A in color, anthers; narrow oblong in shape, 2.5 mm in length, 0.5 mm in width and N199A in color, pollen; moderate in quantity and 17A in color.

*Fruit and seed.*—No fruits or seeds observed to date.

It is claimed:

1. A new and distinct cultivar of *Heliopsis* plant named 'Funky Spinner' as herein illustrated and described.

* * * * *